US012716068B1

(12) United States Patent
Thompson

(10) Patent No.: US 12,716,068 B1
(45) Date of Patent: Aug. 25, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/273,869

(22) Filed: Jul. 18, 2025

(51) Int. Cl.
*C12N 15/113* (2010.01)
*C12N 15/86* (2006.01)

(52) U.S. Cl.
CPC .......... *C12N 15/1137* (2013.01); *C12N 15/86* (2013.01); *C12N 2310/141* (2013.01); *C12N 2750/14143* (2013.01); *C12Y 207/07* (2013.01)

(58) Field of Classification Search
CPC ................ C12N 15/1137; C12N 15/86; C12N 2310/141
See application file for complete search history.

(56) References Cited

U.S. PATENT DOCUMENTS

| | | | |
|---|---|---|---|
| 11,085,055 | B2 | 8/2021 | Mallol et al. |
| 11,162,102 | B2 | 11/2021 | Minshull et al. |
| 11,530,423 | B1 | 12/2022 | Thompson |
| 11,873,505 | B2 | 1/2024 | Thompson |
| 12,018,274 | B2 | 6/2024 | Thompson |
| 12,134,770 | B1 | 11/2024 | Thompson |
| 2024/0026377 | A1 | 1/2024 | Thompson |

FOREIGN PATENT DOCUMENTS

| | | | |
|---|---|---|---|
| CA | 2721333 | A1 | 10/2009 |

OTHER PUBLICATIONS

Chen et al. (Oncol Lett. 2018; 16(1):977-983). (Year: 2018).*
O'Brien et al. (Frontiers in Endocrinology, vol. 9; 2018), (Year: 2018).*
Yu et al. (Cell Mol Immunol. 2021; 18(5):1235-1248). (Year: 2021).*
O'Brien et al. "Overview of microRNA biogenesis, mechanisms of actions, and circulation." Frontiers in endocrinology 9 (2018): 402.
Gorski et al. "RNA-based recognition and targeting: sowing the seeds of specificity." Nature Reviews Molecular Cell Biology 18.4 (2017): 215-228.
Bottoni et al. "Targeting BTK through microRNA in chronic lymphocytic leukemia." Blood, The Journal of the American Society of Hematology 128.26 (2016): 3101-3112.
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016).
Tritschler et al. "Concepts and limitations for learning developmental trajectories from single cell genomics." Development 146.12 (2019): dev170506.
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
Wang et al. "Adeno-associated virus vector as a platform for gene therapy delivery." Nature reviews Drug discovery 18.5 (2019): 358-378.
Kondratov et al. "Direct head-to-head evaluation of recombinant adeno-associated viral vectors manufactured in human versus insect cells." Molecular Therapy 25.12 (2017): 2661-2675.
Nature (2010. Gene Expression. Scitable. Available online at Nature. com) <https://www.nature.com/scitable/topicpage/gene-expression-14121669> (2010).
Brutons Tyrosine Kinase Genbank Sequence (2023).
GenBank EGFR Sequence (2023).
GenBank EGF Sequence (2023).
NCBI search results for SEQ ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
NCBI Nucleotide Sequence for PARP, search performed Dec. 26, 2024 (2024).
GenBank FLT3 Sequence (2024).

* cited by examiner

*Primary Examiner* — J. E. Angell
(74) *Attorney, Agent, or Firm* — Gowling WLG (Canada) LLP

(57) ABSTRACT

The embodiments of the present disclosure relate to one or more compositions or methods that upregulate the production of one or more sequences of micro-interfering ribonucleic acid (miRNA). The sequences of miRNA may be complimentary to a sequence of target messenger RNA (mRNA) that encodes for the translation of a target biomolecule, such as cyclic GMP-AMP synthase (cGAS). The miRNA can cause the target mRNA to be degraded or inactivated, thereby causing a decrease in bioavailability of the target biomolecule because it is degraded or inactivated by the miRNA. Decreasing the bioavailability of the target biomolecule within a subject that is administered the one or more compositions may address the afflictions experienced by the subject due to expression of the target biomolecule.

2 Claims, No Drawings

Specification includes a Sequence Listing.

COMPOSITION FOR REGULATING PRODUCTION OF INTERFERING RIBONUCLEIC ACID

This application contains a Sequence Listing electronically submitted via Patent Center to the United States Patent and Trademark Office as an XML Document file entitled "G10062402P1US-SequenceListing.xml" created on 2025 Jul. 15 and having a size of 15,920 bytes. The information contained in the Sequence Listing is incorporated by reference herein.

TECHNICAL FIELD

The present disclosure generally relates to compositions for regulating the production of micro-interfering ribonucleic acid (miRNA). In particular, the present disclosure relates to compositions for regulating gene expression and therefore, the production of miRNA that will suppress the expression of cyclic GMP-AMP synthase (cGAS).

BACKGROUND

The cGAS-STING pathway is a component of the innate immune system that acts as a sensor for double-stranded (ds) DNA in the cytoplasm of a cell.

When components of the innate immune system are over-expressed or mis-expressed, excessive immune responses can occur.

As such, it may be desirable to establish therapies, treatments and/or interventions that address the loss of regulation of components of the innate immune system in order to prevent or treat the resulting disease caused by excessive immune responses.

SUMMARY

Some embodiments of the present disclosure relate to one or more compositions that upregulate the production of one or more sequences of micro-interfering ribonucleic acid (miRNA). The sequences of miRNA may be complimentary to a sequence of target messenger RNA (mRNA) that encodes for the translation of a target biomolecule, and the miRNA can cause the target mRNA to be degraded or inactivated, thereby causing a decrease in the bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a molecule such as cGAS.

In some embodiments of the present disclosure the compositions comprise a plasmid of deoxyribonucleic acid (DNA) that includes one or more insert sequences of nucleotides that encode for the production of miRNA and a backbone sequence of nucleic acids that facilitates the introduction of the one or more insert sequences into one or more of a subject's cells where it is expressed and/or replicated. Expression of the one or more insert sequences by one or more cells of the subject results in an increased production of the miRNA and, therefore, decreased translation and/or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences that encode a miRNA sequence that targets the mRNA of cGAS.

Some embodiments of the present disclosure relate to a method of making a composition/target cell complex. The method comprises a step of administering an RP comprising SEQ ID NO. 1 and SEQ ID NO. 2 to a target cell in order to form the composition/target cell complex, wherein the composition/target cell complex causes the target cell to increase the production of one or more sequences of miRNA that decreases the production of a target biomolecule.

Embodiments of the present disclosure relate to at least one approach for inducing the endogenous production of one or more sequences of miRNA that target and silence mRNA of a target biomolecule, for example cGAS. A first approach utilizes gene vectors containing nucleotide sequences for increasing the endogenous production of one or more sequences of miRNA, which are complete or partial sequences and/or combinations thereof, that target and silence the mRNA of cGAS, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a kinase that is found within a subject. A biomolecule may be endogenous or exogenous to a subject and when bioavailable the biomolecule may supress, influence or stimulate a physiological process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target biomolecule protein is produced.

In some embodiments of the present disclosure, the target biomolecule is cGAS.

In some embodiments of the present disclosure, the insert comprises one or more nucleotide sequences that each encode one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as cGAS. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as cGAS.

In some embodiments of the present disclosure, the delivery vehicle of the RP used for gene therapy may be a virus that can be enveloped, or not (unenveloped), replication effective, or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ $TCID_{50}$/kg (50% tissue culture infective dose per kilogram of the patient's body mass). In some embodiments of the present disclosure, the therapeutically effective amount of the composition that is administered to the patient is about $1\times10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of an RP that when operable inside a target cell will cause the target cell to produce a miRNA sequence that downregulates the production of a biomolecule, with an example being cGAS. The RP is comprised of AAV2 inverted terminal repeats (ITRs), a composite CASI promoter, a human growth hormone (HGH) signal peptide followed by a miRNA expression cassette containing up to six different miRNAs targeting the mRNA of cGAS, followed by a Woodchuck Hepatitis Virus post-transcriptional regulatory element (WPRE) and an SV40 polyA signal.

```
SEQ ID NO. 1 (backbone sequence No. 1):
5'

ATAATCAACCTCTGGATTACAAAATTTGTGAAAGATTGACTGGTATTCTTAACTATG

TTGCTCCTTTTACGCTATGTGGATACGCTGCTTTAATGCCTTTGTATCATGCTATTGCT

TCCCGTATGGCTTTCATTTTCTCCTCCTTGTATAAATCCTGGTTGCTGTCTCTTTATGA

GGAGTTGTGGCCCGTTGTCAGGCAACGTGGCGTGGTGTGCACTGTGTTTGCTGACGC

AACCCCCACTGGTTGGGGCATTGCCACCACCTGTCAGCTCCTTTCCGGGACTTTCGC

TTTCCCCCTCCCTATTGCCACGGCGGAACTCATCGCCGCCTGCCTTGCCCGCTGCTGG

ACAGGGGCTCGGCTGTTGGGCACTGACAATTCCGTGGTGTTGTCGGGGAAATCATCG

TCCTTTCCTTGGCTGCTCGCCTGTGTTGCCACCTGGATTCTGCGCGGGACGTCCTTCT

GCTACGTCCCTTCGGCCCTCAATCCAGCGGACCTTCCTTCCCGCGGCCTGCTGCCGG

CTCTGCGGCCTCTTCCGCGTCTTCGCCTTCGCCCTCAGACGAGTCGGATCTCCCTTTG

GGCCGCCTCCCCGCCTAAGCTTATCGATACCGTCGAGATCTAACTTGTTTATTGCAG

CTTATAATGGTTACAAATAAAGCAATAGCATCACAAATTTCACAAATAAAGCATTTT

TTTCACTGCATTCTAGTTGTGGTTTGTCCAAACTCATCAATGTATCTTATCATGTCTG

GATCTCGACCTCGACTAGAGCATGGCTACGTAGATAAGTAGCATGGCGGGTTAATC

ATTAACTACAAGGAACCCCTAGTGATGGAGTTGGCCACTCCCTCTCTGCGCGCTCGC

TCGCTCACTGAGGCCGGGCGACCAAAGGTCGCCCGACGCCCGGGCTTTGCCCGGGC

GGCCTCAGTGAGCGAGCGAGCGCGCAGCTGGCGTAATAGCGAAGAGGCCCGCACCG
```

-continued

```
ATCGCCCTTCCCAACAGTTGCGCAGCCTGAATGGCGAATGGCGATTCCGTTGCAATG

GCTGGCGGTAATATTGTTCTGGATATTACCAGCAAGGCCGATAGTTTGAGTTCTTCT

ACTCAGGCAAGTGATGTTATTACTAATCAAAGAAGTATTGCGACAACGGTTAATTTG

CGTGATGGACAGACTCTTTTACTCGGTGGCCTCACTGATTATAAAAACACTTCTCAG

GATTCTGGCGTACCGTTCCTGTCTAAAATCCCTTTAATCGGCCTCCTGTTTAGCTCCC

GCTCTGATTCTAACGAGGAAAGCACGTTATACGTGCTCGTCAAAGCAACCATAGTAC

GCGCCCTGTAGCGGCGCATTAAGCGCGGCGGGTGTGGTGGTTACGCGCAGCGTGAC

CGCTACACTTGCCAGCGCCCTAGCGCCCGCTCCTTTCGCTTTCTTCCCTTCCTTTCTC

GCCACGTTCGCCGGCTTTCCCCGTCAAGCTCTAAATCGGGGGCTCCCTTTAGGGTTC

CGATTTAGTGCTTTACGGCACCTCGACCCCAAAAAACTTGATTAGGGTGATGGTTCA

CGTAGTGGGCCATCGCCCTGATAGACGGTTTTTCGCCCTTTGACGTTGGAGTCCACG

TTCTTTAATAGTGGACTCTTGTTCCAAACTGGAACAACACTCAACCCTATCTCGGTCT

ATTCTTTTGATTTATAAGGGATTTTGCCGATTTCGGCCTATTGGTTAAAAAATGAGCT

GATTTAACAAAAATTTAACGCGAATTTTAACAAAATATTAACGTTTACAATTTAAAT

ATTTGCTTATACAATCTTCCTGTTTTTGGGGCTTTTCTGATTATCAACCGGGGTACAT

ATGATTGACATGCTAGTTTTACGATTACCGTTCATCGATTCTCTTGTTTGCTCCAGAC

TCTCAGGCAATGACCTGATAGCCTTTGTAGAGACCTCTCAAAAATAGCTACCCTCTC

CGGCATGAATTTATCAGCTAGAACGGTTGAATATCATATTGATGGTGATTTGACTGT

CTCCGGCCTTTCTCACCCGTTTGAATCTTTACCTACACATTACTCAGGCATTGCATTT

AAAATATATGAGGGTTCTAAAAATTTTTATCCTTGCGTTGAAATAAAGGCTTCTCCC

GCAAAAGTATTACAGGGTCATAATGTTTTTGGTACAACCGATTTAGCTTTATGCTCT

GAGGCTTTATTGCTTAATTTTGCTAATTCTTTGCCTTGCCTGTATGATTTATTGGATGT

TGGAATTCCTGATGCGGTATTTTCTCCTTACGCATCTGTGCGGTATTTCACACCGCAT

ATGGTGCACTCTCAGTACAATCTGCTCTGATGCCGCATAGTTAAGCCAGCCCCGACA

CCCGCCAACACCCGCTGACGCGCCCTGACGGGCTTGTCTGCTCCCGGCATCCGCTTA

CAGACAAGCTGTGACCGTCTCCGGGAGCTGCATGTGTCAGAGGTTTTCACCGTCATC

ACCGAAACGCGCGAGACGAAAGGGCCTCGTGATACGCCTATTTTTATAGGTTAATGT

CATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAA

TAACCCTGATAAATGCTTCAATAATATTGAAAAAGGAAGAGTATGAGTATTCAACAT

TTCCGTGTCGCCCTTATTCCCTTTTTTGCGGCATTTTGCCTTCCTGTTTTTGCTCACCC

AGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAAC

GTTTTCCAATGATGAGCACTTTTAAAGTTCTGCTATGTGGCGCGGTATTATCCCGTAT

TGACGCCGGGCAAGAGCAACTCGGTCGCCGCATACACTATTCTCAGAATGACTTGGT

TGAGTACTCACCAGTCACAGAAAAGCATCTTACGGATGGCATGACAGTAAGAGAAT

TATGCAGTGCTGCCATAACCATGAGTGATAACACTGCGGCCAACTTACTTCTGACAA

CGATCGGAGGACCGAAGGAGCTAACCGCTTTTTTGCACAACATGGGGGATCATGTA

ACTCGCCTTGATCGTTGGGAACCGGAGCTGAATGAAGCCATACCAAACGACGAGCG

TGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAA
```

-continued

GTTGCAGGACCACTTCTGCGCTCGGCCCTTCCGGCTGGCTGGTTTATTGCTGATAAAT

CTGGAGCCGGTGAGCGTGGGTCTCGCGGTATCATTGCAGCACTGGGGCCAGATGGT

AAGCCCTCCCGTATCGTAGTTATCTACACGACGGGGAGTCAGGCAACTATGGATGA

ACGAAATAGACAGATCGCTGAGATAGGTGCCTCACTGATTAAGCATTGGTAACTGTC

AGACCAAGTTTACTCATATATACTTTAGATTGATTTAAAACTTCATTTTTAATTTAAA

AGGATCTAGGTGAAGATCCTTTTTGATAATCTCATGACCAAAATCCCTTAACGTGAG

TTTTCGTTCCACTGAGCGTCAGACCCCGTAGAAAAGATCAAAGGATCTTCTTGAGAT

CCTTTTTTTCTGCGCGTAATCTGCTGCTTGCAAACAAAAAAACCACCGCTACCAGCG

GTGGTTTGTTTGCCGGATCAAGAGCTACCAACTCTTTTTCCGAAGGTAACTGGCTTC

AGCAGAGCGCAGATACCAAATACTGTCCTTCTAGTGTAGCCGTAGTTAGGCCACCAC

TTCAAGAACTCTGTAGCACCGCCTACATACCTCGCTCTGCTAATCCTGTTACCAGTG

GCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTT

GGAGCGAACGACCTACACCGAACTGAGATACCTACAGCGTGAGCTATGAGAAAGCG

CCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTC

CTGTCGGGTTTCGCCACCTCTGACTTGAGCGTCGATTTTTGTGATGCTCGTCAGGGGG

GCGGAGCCTATGGAAAAACGCCAGCAACGCGGCCTTTTTACGGTTCCTGGCCTTTTG

CTGGCCTTTTGCTCACATGTTCTTTCCTGCGTTATCCCCTGATTCTGTGGATAACCGT

ATTACCGCCTTTGAGTGAGCTGATACCGCTCGCCGCAGCCGAACGACCGAGCGCAG

CGAGTCAGTGAGCGAGGAAGCGGAAGAGCGCCCAATACGCAAACCGCCTCTCCCCG

CGCGTTGGCCGATTCATTAATGCAGCAGCTGCGCGCTCGCTCGCTCACTGAGGCCGC

CCGGGCAAAGCCCGGGCGTCGGGCGACCTTTGGTCGCCCGGCCTCAGTGAGCGAGC

GAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACT

AGTGGAGTTCCGCGTTACATAACTTACGGTAAATGGCCCGCCTGGCTGACCGCCCAA

CGACCCCCGCCCATTGACGTCAATAATGACGTATGTTCCCATAGTAACGCCAATAGG

GACTTTCCATTGACGTCAATGGGTGGAGTATTTACGGTAAACTGCCCACTTGGCAGT

ACATCAAGTGTATCATATGCCAAGTACGCCCCCTATTGACGTCAATGACGGTAAATG

GCCCGCCTGGCATTATGCCCAGTACATGACCTTATGGGACTTTCCTACTTGGCAGTA

CATCTACGTATTAGTCATCGCTATTACCATGGTCGAGGTGAGCCCCACGTTCTGCTTC

ACTCTCCCCATCTCCCCCCCCTCCCCACCCCCAATTTTGTATTTATTTATTTTTTAATT

ATTTTGTGCAGCGATGGGGGCGGGGGGGGGGGGGGGCGCGCGCCAGGCGGGGCGG

GGCGGGGCGAGGGGCGGGGCGGGGCGAGGCGGAGAGGTGCGGCGGCAGCCAATCA

GAGCGGCGCGCTCCGAAAGTTTCCTTTTATGGCGAGGCGGCGGCGGCGGCGGCCCT

ATAAAAAGCGAAGCGCGCGGCGGGCGGGAGTCGCTGCGCGCTGCCTTCGCCCCGTG

CCCCGCTCCGCCGCCGCCTCGCGCCGCCCGCCCCGGCTCTGACTGACCGCGTTACTA

AAACAGGTAAGTCCGGCCTCCGCGCCGGGTTTTGGCGCCTCCCGCGGGCGCCCCCCT

CCTCACGGCGAGCGCTGCCACGTCAGACGAAGGGCGCAGCGAGCGTCCTGATCCTT

CCGCCCGGACGCTCAGGACAGCGGCCCGCTGCTCATAAGACTCGGCCTTAGAACCC

-continued

```
CAGTATCAGCAGAAGGACATTTTAGGACGGGACTTGGGTGACTCTAGGGCACTGGT

TTTCTTTCCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCATGTTCATG

TTTTCTTTTTTTTTCTACAGGTCCTGGGTGACGAACAGGGTACC

3'

SEQ ID NO. 2 (miRNA expression cassette No. 2 - cGAS):
5'

GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGG

AGGCTTGCTGAAGGCTGTATGCTGTCACATGTTCATGTAATAGCTGCGTTTTGGCCTC

TGACTGACGCAGCTATTATGAACATGTGACAGGACACAAGGCCTGTTACTAGCACTC

ACATGGAACAAATGGCCTCTAGCCTGGAGGCTTGCTGAAGGCTGTATGCTGTTCTTT

CGCATATGTTTCGGCACGTTTTGGCCTCTGACTGACGTGCCGAAACATGCGAAAGAA

CAGGACACAAGGCCTGTTACTAGCACTCACATGGAACAAATGGCCTCTAGCCTGGA

GGCTTGCTGAAGGCTGTATGCTGTCATATTCAAAATCTGTTTGGTCGTTTTGGCCTCT

GACTGACGACCAAACAGATTGAATATGACAGGACACAAGGCCTGTTACTAGCACTC

ACATGGAACAAATGGCCTCTCTAGA

3'

SEQ ID NO. 3 = SEQ ID NO. 1 + SEQ ID NO. 2
5'

ATAATCAACCTCTGGATTACAAAATTTGTGAAAGATTGACTGGTATTCTTAACTATG

TTGCTCCTTTTACGCTATGTGGATACGCTGCTTTAATGCCTTTGTATCATGCTATTGCT

TCCCGTATGGCTTTCATTTTCTCCTCCTTGTATAAATCCTGGTTGCTGTCTCTTTATGA

GGAGTTGTGGCCCGTTGTCAGGCAACGTGGCGTGGTGTGCACTGTGTTTGCTGACGC

AACCCCCACTGGTTGGGGCATTGCCACCACCTGTCAGCTCCTTTCCGGGACTTTCGC

TTTCCCCCTCCCTATTGCCACGGCGGAACTCATCGCCGCCTGCCTTGCCCGCTGCTGG

ACAGGGGCTCGGCTGTTGGGCACTGACAATTCCGTGGTGTTGTCGGGGAAATCATCG

TCCTTTCCTTGGCTGCTCGCCTGTGTTGCCACCTGGATTCTGCGCGGGACGTCCTTCT

GCTACGTCCCTTCGGCCCTCAATCCAGCGGACCTTCCTTCCCGCGGCCTGCTGCCGG

CTCTGCGGCCTCTTCCGCGTCTTCGCCTTCGCCCTCAGACGAGTCGGATCTCCCTTTG

GGCCGCCTCCCCGCCTAAGCTTATCGATACCGTCGAGATCTAACTTGTTTATTGCAG

CTTATAATGGTTACAAATAAAGCAATAGCATCACAAATTTCACAAATAAAGCATTTT

TTTCACTGCATTCTAGTTGTGGTTTGTCCAAACTCATCAATGTATCTTATCATGTCTG

GATCTCGACCTCGACTAGAGCATGGCTACGTAGATAAGTAGCATGGCGGGTTAATC

ATTAACTACAAGGAACCCCTAGTGATGGAGTTGGCCACTCCCTCTCTGCGCGCTCGC

TCGCTCACTGAGGCCGGGCGACCAAAGGTCGCCCGACGCCCGGGCTTTGCCCGGGC

GGCCTCAGTGAGCGAGCGAGCGCGCAGCTGGCGTAATAGCGAAGAGGCCCGCACCG

ATCGCCCTTCCCAACAGTTGCGCAGCCTGAATGGCGAATGGCGATTCCGTTGCAATG

GCTGGCGGTAATATTGTTCTGGATATTACCAGCAAGGCCGATAGTTTGAGTTCTTCT

ACTCAGGCAAGTGATGTTATTACTAATCAAAGAAGTATTGCGACAACGGTTAATTTG

CGTGATGGACAGACTCTTTTACTCGGTGGCCTCACTGATTATAAAAACACTTCTCAG

GATTCTGGCGTACCGTTCCTGTCTAAAATCCCTTTAATCGGCCTCCTGTTTAGCTCCC
```

-continued

GCTCTGATTCTAACGAGGAAAGCACGTTATACGTGCTCGTCAAAGCAACCATAGTAC

GCGCCCTGTAGCGGCGCATTAAGCGCGGCGGGTGTGGTGGTTACGCGCAGCGTGAC

CGCTACACTTGCCAGCGCCCTAGCGCCCGCTCCTTTCGCTTTCTTCCCTTCCTTTCTC

GCCACGTTCGCCGGCTTTCCCCGTCAAGCTCTAAATCGGGGGCTCCCTTTAGGGTTC

CGATTTAGTGCTTTACGGCACCTCGACCCCAAAAAACTTGATTAGGGTGATGGTTCA

CGTAGTGGGCCATCGCCCTGATAGACGGTTTTTCGCCCTTTGACGTTGGAGTCCACG

TTCTTTAATAGTGGACTCTTGTTCCAAACTGGAACAACACTCAACCCTATCTCGGTCT

ATTCTTTTGATTTATAAGGGATTTTGCCGATTTCGGCCTATTGGTTAAAAAATGAGCT

GATTTAACAAAAATTTAACGCGAATTTTAACAAAATATTAACGTTTACAATTTAAAT

ATTTGCTTATACAATCTTCCTGTTTTTGGGGCTTTTCTGATTATCAACCGGGGTACAT

ATGATTGACATGCTAGTTTTACGATTACCGTTCATCGATTCTCTTGTTTGCTCCAGAC

TCTCAGGCAATGACCTGATAGCCTTTGTAGAGACCTCTCAAAAATAGCTACCCTCTC

CGGCATGAATTTATCAGCTAGAACGGTTGAATATCATATTGATGGTGATTTGACTGT

CTCCGGCCTTTCTCACCCGTTTGAATCTTTACCTACACATTACTCAGGCATTGCATTT

AAAATATATGAGGGTTCTAAAAATTTTTATCCTTGCGTTGAAATAAAGGCTTCTCCC

GCAAAAGTATTACAGGGTCATAATGTTTTTGGTACAACCGATTTAGCTTTATGCTCT

GAGGCTTTATTGCTTAATTTTGCTAATTCTTTGCCTTGCCTGTATGATTTATTGGATGT

TGGAATTCCTGATGCGGTATTTTCTCCTTACGCATCTGTGCGGTATTTCACACCGCAT

ATGGTGCACTCTCAGTACAATCTGCTCTGATGCCGCATAGTTAAGCCAGCCCCGACA

CCCGCCAACACCCGCTGACGCGCCCTGACGGGCTTGTCTGCTCCCGGCATCCGCTTA

CAGACAAGCTGTGACCGTCTCCGGGAGCTGCATGTGTCAGAGGTTTTCACCGTCATC

ACCGAAACGCGCGAGACGAAAGGGCCTCGTGATACGCCTATTTTTATAGGTTAATGT

CATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAA

TAACCCTGATAAATGCTTCAATAATATTGAAAAAGGAAGAGTATGAGTATTCAACAT

TTCCGTGTCGCCCTTATTCCCTTTTTTGCGGCATTTTGCCTTCCTGTTTTTGCTCACCC

AGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAAC

GTTTTCCAATGATGAGCACTTTTAAAGTTCTGCTATGTGGCGCGGTATTATCCCGTAT

TGACGCCGGGCAAGAGCAACTCGGTCGCCGCATACACTATTCTCAGAATGACTTGGT

TGAGTACTCACCAGTCACAGAAAAGCATCTTACGGATGGCATGACAGTAAGAGAAT

TATGCAGTGCTGCCATAACCATGAGTGATAACACTGCGGCCAACTTACTTCTGACAA

CGATCGGAGGACCGAAGGAGCTAACCGCTTTTTTGCACAACATGGGGGATCATGTA

ACTCGCCTTGATCGTTGGGAACCGGAGCTGAATGAAGCCATACCAAACGACGAGCG

TGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAA

GTTGCAGGACCACTTCTGCGCTCGGCCCTTCCGGCTGGCTGGTTTATTGCTGATAAAT

CTGGAGCCGGTGAGCGTGGGTCTCGCGGTATCATTGCAGCACTGGGGCCAGATGGT

AAGCCCTCCCGTATCGTAGTTATCTACACGACGGGGAGTCAGGCAACTATGGATGA

ACGAAATAGACAGATCGCTGAGATAGGTGCCTCACTGATTAAGCATTGGTAACTGTC

-continued

```
AGACCAAGTTTACTCATATATACTTTAGATTGATTTAAAACTTCATTTTTAATTTAAA
AGGATCTAGGTGAAGATCCTTTTTGATAATCTCATGACCAAAATCCCTTAACGTGAG
TTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCG
GTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCAC
TTCAAGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATAGTTA
CCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTC
CTGTCGGGTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACCGT
ATTACCGCCTTTGAGTGAGCTGATACCGCTCGCCGCAGCCGAACGACCGAGCGCAG
CGAGTCAGTGAGCGAGGAAGCGGAAGAGCGCCCAATACGCAAACCGCCTCTCCCCG
CGCGTTGGCCGATTCATTAATGCAGCAGCTGCGCGCTCGCTCGCTCACTGAGGCCGC
CCGGGCAAAGCCCGGGCGTCGGGCGACCTTTGGTCGCCCGGCCTCAGTGAGCGAGC
GAGCGCGCAGAGAGGGAGTGGCCAACTCCATCACTAGGGGTTCCTTGTAGTTAATG
ATTAACCCGCCATGCTACTTATCTACGTAGCCATGCTCTAGGACATTGATTATTGACT
AGTGGAGTTCCGCGTTACATAACTTACGGTAAATGGCCCGCCTGGCTGACCGCCCAA
CGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAATG
GCCCGCCTGGCATTATGCCCAGTACATGACCTTATGGGACTTTCCTACTTGGCAGTA
CATCTACGTATTAGTCATCGCTATTACCATGGTCGAGGTGAGCCCCACGTTCTGCTTC
ACTCTCCCCATCTCCCCCCCCTCCCCACCCCCAATTTTGTATTTATTTATTTTTTAATT
ATTTTGTGCAGCGATGGGGGCGGGGGGGGGGGGGGCGCGCGCCAGGCGGGGCGG
GGCGGGGCGAGGGGCGGGGCGGGGCGAGGCGGAGAGGTGCGGCGGCAGCCAATCA
GAGCGGCGCGCTCCGAAAGTTTCCTTTTATGGCGAGGCGGCGGCGGCGGCGGCCCT
ATAAAAAGCGAAGCGCGCGGCGGGCGGGAGTCGCTGCGCGCTGCCTTCGCCCCGTG
CCCCGCTCCGCCGCCGCCTCGCGCCGCCCGCCCCGGCTCTGACTGACCGCGTTACTA
AAACAGGTAAGTCCGGCCTCCGCGCCGGGTTTTGGCGCCTCCCGCGGGCGCCCCCCT
CCTCACGGCGAGCGCTGCCACGTCAGACGAAGGGCGCAGCGAGCGTCCTGATCCTT
CCGCCCGGACGCTCAGGACAGCGGCCCGCTGCTCATAAGACTCGGCCTTAGAACCC
CAGTATCAGCAGAAGGACATTTTAGGACGGGACTTGGGTGACTCTAGGGCACTGGT
TTTCTTTCCAGAGAGCGGAACAGGCGAGGAAAAGTAGTCCCTTCTCGGCGATTCTGC
GGAGGGATCTCCGTGGGGCGGTGAACGCCGATGATGCCTCTACTAACCATGTTCATG
TTTTCTTTTTTTTTCTACAGGTCCTGGGTGACGAACAGGGTACCGCCACCATGGCCAC
CGGCTCTCGCACAAGCCTGCTGCTGGCTTTCGGACTGCTGTGCCTGCCTTGGCTCCA
```

-continued

```
GGAGGGCTCCGCCGCTAGCATCGATACCGTCGCTATGTGCTGGAGGCTTGCTGAAGG

CTGTATGCTGTCACATGTTCATGTAATAGCTGCGTTTTGGCCTCTGACTGACGCAGCT

ATTATGAACATGTGACAGGACACAAGGCCTGTTACTAGCACTCACATGGAACAAAT

GGCCTCTAGCCTGGAGGCTTGCTGAAGGCTGTATGCTGTTCTTTCGCATATGTTTCGG

CACGTTTTGGCCTCTGACTGACGTGCCGAAACATGCGAAAGAACAGGACACAAGGC

CTGTTACTAGCACTCACATGGAACAAATGGCCTCTAGCCTGGAGGCTTGCTGAAGGC

TGTATGCTGTCATATTCAAAATCTGTTTGGTCGTTTTGGCCTCTGACTGACGACCAAA

CAGATTGAATATGACAGGACACAAGGCCTGTTACTAGCACTCACATGGAACAAATG

GCCTCTCTAGA

3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands of interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

Example 2—In Vitro Studies

To confirm that the recombinant plasmid of Example 1 works to downregulate cGAS expression, HEK293 cells were treated with either a first plasmid (First Treatment) or the first plasmid and a second plasmid (collectively, the Second Treatment).

The First Treatment comprised the first plasmid with a nucleotide sequence that codes for the backbone nucleotide sequence No. 1 (described herein as SEQ ID NO. 1) and a nucleotide sequence that codes for the expression of cGAS mRNA of the sequence defined in Uniprot Q8N884.CGAS_HUMAN. HEK293 cells do not produce substantial amounts of cGAS on their own and, therefore, the purpose of the First Treatment was to cause the HEK293 cells to produce enough cGAS so that any decrease in cGAS production caused by the Second Treatment could be detected.

The Second Treatment comprised the first plasmid (which included the nucleotide sequence of SEQ ID NO. 1 and a nucleotide sequence that codes for expression of cGAS mRNA) and a second plasmid that codes for the backbone nucleotide sequence SEQ ID NO. 1 and a nucleotide sequence of the micro-interfering RNA (miRNA) for cGAS (described herein as SEQ ID NO. 2). The SEQ ID NO. 2 codes for a miRNA sequence that is designed to bind to and inactivate the messenger ribonucleic acid (mRNA) of cGAS.

Briefly, the HEK293 cells were seeded in 96-wellplates in Dulbecco's Modified Eagle Medium (DMEM)/10% Fetal Bovine Serum (FBS) media. 24 hours later, the cells were treated with either the First Treatment or the Second Treatment. A transfection mixture containing OptiMEM (reduced serum medium, commercially available from Gibco), plasmid DNA, and PEI max (Transfection Grade Linear Polyethylenimine Hydrochloride (MW 40,000), commercially available from Polysciences) was prepared in a sterile 1 mL conical tube and incubated at room temperature for 10 minutes prior to adding 100 μL of the mixture to each seeded well (100 μL/well equals about 1 ug of each plasmid per well).

72 hours post-treatment, the cells were harvested by separating the cells from the well surface with 2.9 mM ethylenediaminetetraacetic acid (EDTA) and centrifuging the resulting cell suspension into a cell pellet. The cell pellet was lysed, and 40 μg of protein (as assayed by the Lowry assay) was loaded into sodium dodecyl sulfate-polyacrylamide (SDS PAGE) gels for molecular weight electrophoretic separation. A total of eight gel lanes were loaded with the protein obtained from the wells treated with the First Treatment and eight gel lanes were loaded with the protein obtained from the wells treated with the Second Treatment. The band approximating 58,814 Daltons (the molecular weight of the cGAS amino acid sequence), was excised from each lane, eluted, and the protein amount was assayed by the Lowry method.

The average expression levels of cGAS (ug) measured in HEK293 cells treated with the First Treatment (that encoded for cGAS mRNA) was 7.2 μg. The average expression levels in the HEK293 cells treated with the Second Treatment (that encoded for SEQ ID NO. 2) was less than 1 μg, which is below the lower detection limit of the Lowry assay. The amounts of measured protein were significantly different, as assessed by a two-way T-test ($p<0.001$), using 1 ug as the value for the expression levels in the HEK293 cells treated with the Second Treatment.

This data demonstrates that the HEK293 cells treated with the First Treatment were successfully transfected causing the cells to produce cGAS, a protein HEK293 cells typically do not produce in vitro without any treatment. The data above also demonstrates that the HEK293 cells treated with the Second Treatment produced significantly less cGAS.

Without being bound by any particular theory, this data demonstrates the efficacy of miRNA-based gene silencing of cGAS protein expression by using the Second Treatment, which included the miRNA encoded by SEQ ID NO. 2.

The invention claimed is:

1. A composition that comprises a recombinant plasmid (RP) that comprises a sequence that is SEQ ID NO. 2.

2. The composition of claim 1, wherein the sequence of nucleotides is encapsulated in a protein coat, a lipid vesicle, or any combination thereof.

* * * * *

SEQUENCE LISTING

```
Sequence total quantity: 3
SEQ ID NO: 1           moltype = DNA  length = 5801
FEATURE                Location/Qualifiers
source                 1..5801
                       mol_type = other DNA
                       organism = synthetic construct
SEQUENCE: 1
ataatcaacc tctggattac aaaatttgtg aaagattgac tggtattctt aactatgttg  60
ctccttttac gctatgtgga tacgctgctt taatgccttt gtatcatgct attgcttccc  120
gtatggcttt cattttctcc tccttgtata aatcctggtt gctgtctctt tatgaggagt  180
tgtggcccgt tgtcaggcaa cgtggcgtgg tgtgcactgt gtttgctgac gcaaccccca  240
ctggttgggg cattgccacc acctgtcagc tcctttccgg gactttcgct ttccccctcc  300
ctattgccac ggcggaactc atcgccgcct gccttgcccg ctgctggaca ggggctcggc  360
tgttgggcac tgacaattcc gtggtgttgt cggggaaatc atcgtccttt ccttggctgc  420
tcgcctgtgt tgccacctgg attctgcgcg ggacgtcctt ctgctacgtc ccttcggccc  480
tcaatccagc ggaccttcct tcccgcggcc tgctgccggc tctgcggcct cttccgcgtc  540
ttcgccttcg ccctcagacg agtcggatct ccctttgggc cgcctccccg cctaagctta  600
tcgataccgt cgagatctaa cttgtttatt gcagcttata atggttacaa ataaagcaat  660
agcatcacaa atttcacaaa taaagcattt ttttcactgc attctagttg tggtttgtcc  720
aaactcatca atgtatctta tcatgtctgg atctcgacct cgactagagc atggctacgt  780
agataagtag catggcgggt taatcattaa ctacaaggaa cccctagtga tggagttggc  840
cactccctct ctgcgcgctc gctcgctcac tgaggccggg cgaccaaagg tcgcccgacg  900
cccgggcttt gcccgggcgg cctcagtgag cgagcgagcg cgcagctggc gtaatagcga  960
agaggcccgc accgatcgcc cttcccaaca gttgcgcagc ctgaatggcg aatggcgatt  1020
ccgttgcaat ggctggcggt aatattgttc tggatattac cagcaaggcc gatagtttga  1080
gttcttctac tcaggcaagt gatgttatta ctaatcaaag aagtattgcg acaacggtta  1140
atttgcgtga tggacagact cttttactcg gtggcctcac tgattataaa aacacttctc  1200
aggattctgg cgtaccgttc ctgtctaaaa tccctttaat cggcctcctg tttagctccc  1260
gctctgattc taacgaggaa agcacgttat acgtgctcgt caaagcaacc atagtacgcg  1320
ccctgtagcg gcgcattaag cgcggcgggt gtggtggtta cgcgcagcgt gaccgctaca  1380
cttgccagcg ccctagcgcc cgctcctttc gctttcttcc cttcctttct cgccacgttc  1440
gccggctttc cccgtcaagc tctaaatcgg gggctccctt tagggttccg atttagtgct  1500
ttacggcacc tcgaccccaa aaaacttgat tagggtgatg gttcacgtag tgggccatcg  1560
ccctgataga cggtttttcg ccctttgacg ttggagtcca cgttctttaa tagtggactc  1620
ttgttccaaa ctggaacaac actcaaccct atctcggtct attcttttga tttataaggg  1680
attttgccga tttcggccta ttggttaaaa aatgagctga tttaacaaaa atttaacgcg  1740
aattttaaca aaatattaac gtttacaatt taaatatttg cttatacaat cttcctgttt  1800
ttggggcttt tctgattatc aaccggggta catatgattg acatgctagt tttacgatta  1860
ccgttcatcg attctcttgt ttgctccaga ctctcaggca atgacctgat agcctttgta  1920
gagacctctc aaaaatagct accctctccg gcatgaattt atcagctaga acggttgaat  1980
atcatattga tggtgatttg actgtctccg gcctttctca cccgtttgaa tctttaccta  2040
cacattactc aggcattgca tttaaaatat atgagggttc taaaaatttt tatccttgcg  2100
ttgaaataaa ggcttctccc gcaaaagtat tacagggtca taatgttttt ggtacaaccg  2160
atttagcttt atgctctgag gctttattgc ttaattttgc taattctttg ccttgcctgt  2220
atgatttatt ggatgttgga attcctgatg cggtattttc tccttacgca tctgtgcggt  2280
atttcacacc gcatatggtg cactctcagt acaatctgct ctgatgccgc atagttaagc  2340
cagccccgac acccgccaac acccgctgac gcgccctgac gggcttgtct gctcccggca  2400
tccgcttaca gacaagctgt gaccgtctcc gggagctgca tgtgtcagag gttttcaccg  2460
tcatcaccga aacgcgcgag acgaaagggc ctcgtgatac gcctattttt ataggttaat  2520
gtcatgataa taatggtttc ttagacgtca ggtggcactt ttcggggaaa tgtgcgcgga  2580
acccctattt gtttattttt ctaaatacat tcaaatatgt atccgctcat gagacaataa  2640
ccctgataaa tgcttcaata atattgaaaa aggaagagta tgagtattca acatttccgt  2700
gtcgccctta ttcccttttt tgcggcattt tgccttcctg tttttgctca cccagaaacg  2760
ctggtgaaag taaaagatgc tgaagatcag ttgggtgcac gagtgggtta catcgaactg  2820
gatctcaaca gcggtaagat ccttgagagt tttcgccccg aagaacgttt tccaatgatg  2880
agcactttta aagttctgct atgtggcgcg gtattatccc gtattgacgc cgggcaagag  2940
caactcggtc gccgcataca ctattctcag aatgacttgg ttgagtactc accagtcaca  3000
```

```
gaaaagcatc ttacggatgg catgacagta agagaattat gcagtgctgc cataaccatg  3060
agtgataaca ctgcggccaa cttacttctg acaacgatcg gaggaccgaa ggagctaacc  3120
gcttttttgc acaacatggg ggatcatgta actcgccttg atcgttggga accggagctg  3180
aatgaagcca taccaaacga cgagcgtgac accacgatgc ctgtagcaat ggcaacaacg  3240
ttgcgcaaac tattaactgg cgaactactt actctagctt cccggcaaca attaatagac  3300
tggatggagg cggataaagt tgcaggacca cttctgcgct cggcccttcc ggctggctgg  3360
tttattgctg ataaatctgg agccggtgag cgtgggtctc gcggtatcat tgcagcactg  3420
gggccagatg gtaagccctc ccgtatcgta gttatctaca cgacggggag tcaggcaact  3480
atggatgaac gaaatagaca gatcgctgag ataggtgcct cactgattaa gcattggtaa  3540
ctgtcagacc aagtttactc atatatactt tagattgatt taaaacttca tttttaattt  3600
aaaaggatct aggtgaagat cctttttgat aatctcatga ccaaaatccc ttaacgtgag  3660
ttttcgttcc actgagcgtc agaccccgta gaaaagatca aaggatcttc ttgagatcct  3720
ttttttctgc gcgtaatctg ctgcttgcaa acaaaaaaac caccgctacc agcggtggtt  3780
tgtttgccgg atcaagagct accaactctt tttccgaagg taactggctt cagcagagcg  3840
cagataccaa atactgtcct tctagtgtag ccgtagttag gccaccactt caagaactct  3900
gtagcaccgc ctacatacct cgctctgcta atcctgttac cagtggctgc tgccagtggc  3960
gataagtcgt gtcttaccgg gttggactca agacgatagt taccggataa ggcgcagcgg  4020
tcgggctgaa cggggggttc gtgcacacag cccagcttgg agcgaacgac ctacaccgaa  4080
ctgagatacc tacagcgtga gctatgagaa agcgccacgc ttcccgaagg gagaaaggcg  4140
gacaggtatc cggtaagcgg cagggtcgga acaggagagc gcacgaggga gcttccaggg  4200
ggaaacgcct ggtatcttta tagtcctgtc gggtttcgcc acctctgact tgagcgtcga  4260
tttttgtgat gctcgtcagg ggggcggagc ctatggaaaa acgccagcaa cgcggccttt  4320
ttacggttcc tggccttttg ctggcctttt gctcacatgt tctttcctgc gttatcccct  4380
gattctgtgg ataaccgtat taccgccttt gagtgagctg ataccgctcg ccgcagccga  4440
acgaccgagc gcagcgagtc agtgagcgag gaagcggaag agcgcccaat acgcaaaccg  4500
cctctccccg cgcgttggcc gattcattaa tgcagcagct gcgcgctcgc tcgctcactg  4560
aggccgcccg ggcaaagccc gggcgtcggg cgacctttgg tcgcccggcc tcagtgagcg  4620
agcgagcgcg cagagaggga gtggccaact ccatcactag gggttccttg tagttaatga  4680
ttaacccgcc atgctactta tctacgtagc catgctctag gacattgatt attgactagt  4740
ggagttccgc gttacataac ttacggtaaa tggcccgcct ggctgaccgc ccaacgaccc  4800
ccgcccattg acgtcaataa tgacgtatgt tcccatagta acgccaatag ggactttcca  4860
ttgacgtcaa tgggtggagt atttacggta aactgcccac ttggcagtac atcaagtgta  4920
tcatatgcca agtacgcccc ctattgacgt caatgacggt aaatggcccg cctggcatta  4980
tgcccagtac atgaccttat gggactttcc tacttggcag tacatctacg tattagtcat  5040
cgctattacc atggtcgagg tgagccccac gttctgcttc actctcccca tctccccccc  5100
ctccccaccc ccaattttgt atttatttat tttttaatta ttttgtgcag cgatgggggc  5160
gggggggggg ggggggcgcgc gccaggcggg gcggggcggg gcgaggggcg gggcggggcg  5220
aggcggagag gtgcggcggc agccaatcag agcggcgcgc tccgaaagtt tccttttatg  5280
gcgaggcggc ggcggcggcg gccctataaa aagcgaagcg cgcggcgggc gggagtcgct  5340
gcgcgctgcc ttcgccccgt gccccgctcc gccgccgcct cgcgccgccc gccccggctc  5400
tgactgaccg cgttactaaa acaggtaagt ccggcctccg cgccgggttt tggcgcctcc  5460
cgcgggcgcc cccctcctca cggcgagcgc tgccacgtca gacgaagggc gcagcgagcg  5520
tcctgatcct tccgcccgga cgctcaggac agcggcccgc tgctcataag actcggcctt  5580
agaaccccag tatcagcaga aggacatttt aggacgggac ttgggtgact ctagggcact  5640
ggttttcttt ccagagagcg gaacaggcga ggaaaagtag tcccttctcg gcgattctgc  5700
ggagggatct ccgtggggcg gtgaacgccg atgatgcctc tactaaccat gttcatgttt  5760
tctttttttt tctacaggtc ctgggtgacg aacagggtac c                       5801
```

```
SEQ ID NO: 2            moltype = DNA  length = 538
FEATURE                 Location/Qualifiers
source                  1..538
                        mol_type = other DNA
                        organism = synthetic construct
SEQUENCE: 2
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgtc acatgttcat gtaatagctg cgttttggcc tctgactgac  180
gcagctatta tgaacatgtg acaggacaca aggcctgtta ctagcactca catggaacaa  240
atggcctcta gcctggaggc ttgctgaagg ctgtatgctg ttctttcgca tatgtttcgg  300
cacgttttgg cctctgactg acgtgccgaa acatgcgaaa gaacaggaca caaggcctgt  360
tactagcact cacatggaac aaatggcctc tagcctggag gcttgctgaa ggctgtatgc  420
tgtcatattc aaaatctgtt tggtcgtttt ggcctctgac tgacgaccaa acagattgaa  480
tatgacagga cacaaggcct gttactagca ctcacatgga acaaatggcc tctctaga    538
```

```
SEQ ID NO: 3            moltype = DNA  length = 6339
FEATURE                 Location/Qualifiers
source                  1..6339
                        mol_type = other DNA
                        organism = synthetic construct
SEQUENCE: 3
ataatcaacc tctggattac aaaatttgtg aaagattgac tggtattctt aactatgttg  60
ctccttttac gctatgtgga tacgctgctt taatgccttt gtatcatgct attgcttccc  120
gtatggcttt cattttctcc tccttgtata aatcctggtt gctgtctctt tatgaggagt  180
tgtggcccgt tgtcaggcaa cgtggcgtgg tgtgcactgt gtttgctgac gcaaccccca  240
ctggttgggg cattgccacc acctgtcagc tcctttccgg gactttcgct ttccccctcc  300
ctattgccac ggcggaactc atcgccgcct gccttgcccg ctgctggaca ggggctcggc  360
tgttgggcac tgacaattcc gtggtgttgt cggggaaatc atcgtccttt ccttggctgc  420
tcgcctgtgt tgccacctgg attctgcgcg ggacgtcctt ctgctacgtc ccttcggccc  480
tcaatccagc ggaccttcct tcccgcggcc tgctgccggc tctgcggcct cttccgcgtc  540
```

-continued

```
ttcgccttcg ccctcagacg agtcggatct ccctttgggc cgcctccccg cctaagctta  600
tcgataccgt cgagatctaa cttgtttatt gcagcttata atggttacaa ataaagcaat  660
agcatcacaa atttcacaaa taaagcattt ttttcactgc attctagttg tggtttgtcc  720
aaactcatca atgtatctta tcatgtctgg atctcgacct cgactagagc atggctacgt  780
agataagtag catggcgggt taatcattaa ctacaaggaa cccctagtga tggagttggc  840
cactccctct ctgcgcgctc gctcgctcac tgaggccggg cgaccaaagg tcgcccgacg  900
cccgggcttt gcccgggcgg cctcagtgag cgagcgagcg cgcagctggc gtaatagcga  960
agaggcccgc accgatcgcc cttcccaaca gttgcgcagc ctgaatggcg aatggcgatt  1020
ccgttgcaat ggctggcggt aatattgttc tggatattac cagcaaggcc gatagtttga  1080
gttcttctac tcaggcaagt gatgttatta ctaatcaaag aagtattgcg acaacggtta  1140
atttgcgtga tggacagact cttttactcg gtggcctcac tgattataaa aacacttctc  1200
aggattctgg cgtaccgttc ctgtctaaaa tccctttaat cggcctcctg tttagctccc  1260
gctctgattc taacgaggaa agcacgttat acgtgctcgt caaagcaacc atagtacgcg  1320
ccctgtagcg gcgcattaag cgcggcgggt gtggtggtta cgcgcagcgt gaccgctaca  1380
cttgccagcg ccctagcgcc cgctcctttc gctttcttcc cttcctttct cgccacgttc  1440
gccggctttc cccgtcaagc tctaaatcgg gggctccctt tagggttccg atttagtgct  1500
ttacggcacc tcgaccccaa aaaacttgat tagggtgatg gttcacgtag tgggccatcg  1560
ccctgataga cggtttttcg ccctttgacg ttggagtcca cgttctttaa tagtggactc  1620
ttgttccaaa ctggaacaac actcaaccct atctcggtct attcttttga tttataaggg  1680
attttgccga tttcggccta ttggttaaaa aatgagctga tttaacaaaa atttaacgcg  1740
aattttaaca aaatattaac gtttacaatt taaatatttg cttatacaat cttcctgttt  1800
ttggggcttt tctgattatc aaccggggta catatgattg acatgctagt tttacgatta  1860
ccgttcatcg attctcttgt ttgctccaga ctctcaggca atgacctgat agcctttgta  1920
gagacctctc aaaaatagct accctctccg gcatgaattt atcagctaga acggttgaat  1980
atcatattga tggtgatttg actgtctccg gcctttctca cccgtttgaa tctttaccta  2040
cacattactc aggcattgca tttaaaatat atgagggttc taaaaatttt tatccttgcg  2100
ttgaaataaa ggcttctccc gcaaaagtat tacagggtca taatgttttt ggtacaaccg  2160
atttagcttt atgctctgag gctttattgc ttaattttgc taattctttg ccttgcctgt  2220
atgatttatt ggatgttgga attcctgatg cggtattttc tccttacgca tctgtgcggt  2280
atttcacacc gcatatggtg cactctcagt acaatctgct ctgatgccgc atagttaagc  2340
cagccccgac acccgccaac acccgctgac gcgccctgac gggcttgtct gctcccggca  2400
tccgcttaca gacaagctgt gaccgtctcc gggagctgca tgtgtcagag gttttcaccg  2460
tcatcaccga aacgcgcgag acgaaagggc ctcgtgatac gcctattttt ataggttaat  2520
gtcatgataa taatggtttc ttagacgtca ggtggcactt ttcggggaaa tgtgcgcgga  2580
acccctattt gtttattttt ctaaatacat tcaaatatgt atccgctcat gagacaataa  2640
ccctgataaa tgcttcaata atattgaaaa aggaagagta tgagtattca acatttccgt  2700
gtcgccctta ttcccttttt tgcggcattt tgccttcctg tttttgctca cccagaaacg  2760
ctggtgaaag taaaagatgc tgaagatcag ttgggtgcac gagtgggtta catcgaactg  2820
gatctcaaca gcggtaagat ccttgagagt tttcgccccg aagaacgttt tccaatgatg  2880
agcactttta aagttctgct atgtggcgcg gtattatccc gtattgacgc cgggcaagag  2940
caactcggtc gccgcataca ctattctcag aatgacttgg ttgagtactc accagtcaca  3000
gaaaagcatc ttacggatgg catgacagta agagaattat gcagtgctgc cataaccatg  3060
agtgataaca ctgcggccaa cttacttctg acaacgatcg gaggaccgaa ggagctaacc  3120
gcttttttgc acaacatggg ggatcatgta actcgccttg atcgttggga accggagctg  3180
aatgaagcca taccaaacga cgagcgtgac accacgatgc ctgtagcaat ggcaacaacg  3240
ttgcgcaaac tattaactgg cgaactactt actctagctt cccggcaaca attaatagac  3300
tggatggagg cggataaagt tgcaggacca cttctgcgct cggcccttcc ggctggctgg  3360
tttattgctg ataaatctgg agccggtgag cgtgggtctc gcggtatcat tgcagcactg  3420
gggccagatg gtaagccctc ccgtatcgta gttatctaca cgacggggag tcaggcaact  3480
atggatgaac gaaatagaca gatcgctgag ataggtgcct cactgattaa gcattggtaa  3540
ctgtcagacc aagtttactc atatatactt tagattgatt taaaacttca tttttaattt  3600
aaaaggatct aggtgaagat cctttttgat aatctcatga ccaaaatccc ttaacgtgag  3660
ttttcgttcc actgagcgtc agaccccgta gaaaagatca aaggatcttc ttgagatcct  3720
ttttttctgc gcgtaatctg ctgcttgcaa acaaaaaaac caccgctacc agcggtggtt  3780
tgtttgccgg atcaagagct accaactctt tttccgaagg taactggctt cagcagagcg  3840
cagataccaa atactgtcct tctagtgtag ccgtagttag gccaccactt caagaactct  3900
gtagcaccgc ctacatacct cgctctgcta atcctgttac cagtggctgc tgccagtggc  3960
gataagtcgt gtcttaccgg gttggactca agacgatagt taccggataa ggcgcagcgg  4020
tcgggctgaa cggggggttc gtgcacacag cccagcttgg agcgaacgac ctacaccgaa  4080
ctgagatacc tacagcgtga gctatgagaa agcgccacgc ttcccgaagg gagaaaggcg  4140
gacaggtatc cggtaagcgg cagggtcgga acaggagagc gcacgaggga gcttccaggg  4200
ggaaacgcct ggtatcttta tagtcctgtc gggtttcgcc acctctgact tgagcgtcga  4260
tttttgtgat gctcgtcagg ggggcggagc ctatggaaaa acgccagcaa cgcggccttt  4320
ttacggttcc tggccttttg ctggcctttt gctcacatgt tctttcctgc gttatcccct  4380
gattctgtgg ataaccgtat taccgccttt gagtgagctg ataccgctcg ccgcagccga  4440
acgaccgagc gcagcgagtc agtgagcgag gaagcggaag agcgcccaat acgcaaaccg  4500
cctctccccg cgcgttggcc gattcattaa tgcagcagct gcgcgctcgc tcgctcactg  4560
aggccgcccg ggcaaagccc gggcgtcggg cgacctttgg tcgcccggcc tcagtgagcg  4620
agcgagcgcg cagagaggga gtggccaact ccatcactag gggttccttg tagttaatga  4680
ttaacccgcc atgctactta tctacgtagc catgctctag gacattgatt attgactagt  4740
ggagttccgc gttacataac ttacggtaaa tggcccgcct ggctgaccgc ccaacgaccc  4800
ccgcccattg acgtcaataa tgacgtatgt tcccatagta acgccaatag ggactttcca  4860
ttgacgtcaa tgggtggagt atttacggta aactgcccac ttggcagtac atcaagtgta  4920
tcatatgcca agtacgcccc ctattgacgt caatgacggt aaatggcccg cctggcatta  4980
tgcccagtac atgaccttat gggactttcc tacttggcag tacatctacg tattagtcat  5040
cgctattacc atggtcgagg tgagccccac gttctgcttc actctcccca tctccccccc  5100
ctccccaccc ccaattttgt atttatttat tttttaatta ttttgtgcag cgatgggggc  5160
gggggggggg gggggcgcgc gccaggcggg gcggggcggg gcgaggggcg gggcggggcg  5220
aggcggagag gtgcggcggc agccaatcag agcggcgcgc tccgaaagtt tccttttatg  5280
```

-continued

```
gcgaggcggc ggcggcggcg gccctataaa aagcgaagcg cgcggcgggc gggagtcgct  5340
gcgcgctgcc ttcgccccgt gccccgctcc gccgccgcct cgcgccgccc gccccggctc  5400
tgactgaccg cgttactaaa acaggtaagt ccggcctccg cgccgggttt tggcgcctcc  5460
cgcgggcgcc cccctcctca cggcgagcgc tgccacgtca gacgaagggc gcagcgagcg  5520
tcctgatcct tccgcccgga cgctcaggac agcggcccgc tgctcataag actcggcctt  5580
agaaccccag tatcagcaga aggacatttt aggacgggac ttgggtgact ctagggcact  5640
ggttttcttt ccagagagcg gaacaggcga ggaaaagtag tcccttctcg gcgattctgc  5700
ggagggatct ccgtggggcg gtgaacgccg atgatgcctc tactaaccat gttcatgttt  5760
tctttttttt tctacaggtc ctgggtgacg aacagggtac cgccaccatg gccaccggct  5820
ctcgcacaag cctgctgctg gctttcggac tgctgtgcct gccttggctc caggagggct  5880
ccgccgctag catcgatacc gtcgctatgt gctggaggct tgctgaaggc tgtatgctgt  5940
cacatgttca tgtaatagct gcgttttggc ctctgactga cgcagctatt atgaacatgt  6000
gacaggacac aaggcctgtt actagcactc acatggaaca aatggcctct agcctggagg  6060
cttgctgaag gctgtatgct gttctttcgc atatgtttcg gcacgttttg gcctctgact  6120
gacgtgccga aacatgcgaa agaacaggac acaaggcctg ttactagcac tcacatggaa  6180
caaatggcct ctagcctgga ggcttgctga aggctgtatg ctgtcatatt caaaatctgt  6240
ttggtcgttt tggcctctga ctgacgacca aacagattga atatgacagg acacaaggcc  6300
tgttactagc actcacatgg aacaaatggc ctctctaga                        6339
```